United States Patent [19]

Wolf

[11] 4,315,767
[45] Feb. 16, 1982

[54] TRIAZOLONE HERBICIDES

[75] Inventor: Anthony D. Wolf, Newark, Del.

[73] Assignee: E. I. Du Pont de Nemours and Company, Wilmington, Del.

[21] Appl. No.: 103,958

[22] Filed: Dec. 14, 1979

Related U.S. Application Data

[62] Division of Ser. No. 926,120, Jul. 19, 1978, Pat. No. 4,214,891, which is a division of Ser. No. 823,204, Aug. 9, 1977, Pat. No. 4,139,364.

[51] Int. Cl.³ .................. A01N 43/02; C07D 513/00; C07D 513/02
[52] U.S. Cl. ............................................ 71/91; 71/90; 544/48; 548/154; 260/245.5
[58] Field of Search ...................... 544/48; 71/92, 91; 548/154; 260/245.5

[56] References Cited

U.S. PATENT DOCUMENTS

| | | | |
|---|---|---|---|
| 3,932,395 | 1/1976 | Hideg et al. | 544/48 |
| 4,042,373 | 8/1977 | Moje | 71/91 |
| 4,049,418 | 9/1977 | Timmler et al. | 71/92 |
| 4,066,437 | 1/1978 | Von Bredow | 71/91 |
| 4,069,035 | 1/1978 | Johnson | 71/92 |
| 4,179,276 | 12/1979 | Cheng | 544/48 |

Primary Examiner—Glennon H. Hollrah

[57] ABSTRACT

Triazolone herbicides of the formula:

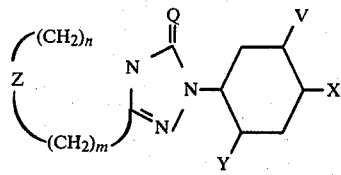

where
V is hydrogen, fluorine, chlorine, bromine, methyl or OR where R is alkyl of 1–4 carbon atoms;
X is hydrogen, fluorine, chlorine, bromine, cyano, methyl, methoxy, or nitro;
Y is hydrogen, fluorine, chlorine, bromine, or methyl;
n, m is 0, 1, 2, 3 or 4;
Q is oxygen or sulfur;
Z is oxygen, $S(O)_p$ or NR';
p is 0, 1 or 2 and
R' is alkyl of 1–3 carbon atoms with the provisos that
(1) n+m=2, 3, or 4; and
(2) if n+m=2 or 4 then Y, X≠H
and when Z is $S(O)p$, n is 1, 2, 3 or 4.

13 Claims, No Drawings

TRIAZOLONE HERBICIDES

This is a division, of application Ser. No. 926,120, filed on July 19, 1978 now U.S. Pat. No. 4,214,891 in turn is a division of application Ser. No. 823,204, filed on Aug. 9, 1977, (now U.S. Pat. No. 4,139,364).

BACKGROUND OF THE INVENTION

West German Application No. 1,948,793, dated Sept. 26, 1969, discloses a method for preparation of a broad general class of 4,5,6,7-tetrahydroindazoles which are useful intermediates in the preparation of pharmaceuticals, agricultural chemicals and corrosion inhibitors.

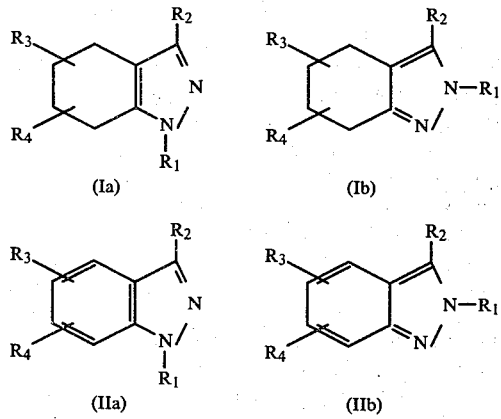

Specifically disclosed is the preparation of Compound Ib, where $R_2$, $R_3$, and $R_4$ are hydrogen and $R_1$ is phenyl, from Compound IIb (same substitution) by catalytic reduction.

The preparation and fungicidal utility of the 2-p-chlorophenylindazol-3-one is disclosed in Takeda Chem. Ind. Paper, Chem. Abs., 67, 11542h (1967):

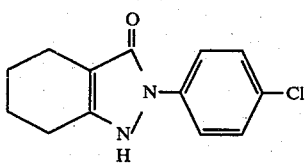

2-Aryl-4,5,6,7-tetrahydro-1-alkyl-1H-indazol-3(2H)-ones are claimed as antipyretics in Ger. 668,628 [assigned to P. Beierdorf & Co. AG, Chem. Abs., 33, 5131[2] (1939)] and U.S. Pat No. 2,104,348 [assigned to E. R. Squibb Co., Chem. Abs., 32, 1869[1] (1938)].

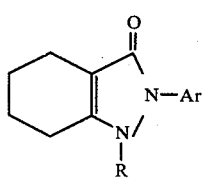

1-Phenyl-3,4-trimethylenepyrazolone is disclosed in U.S. Pat. No. 1,685,407 (1928) with utility as intermediate for making dyes and medicinal compounds. C. Mannich in Arch. Pharm. 267, 699–702 (1929) and in Brit. No. 260,577 describes the preparation of 1-phenyl-3,4-trimethylenepyrazolones.

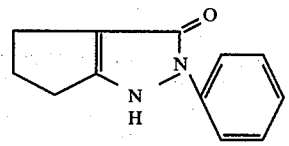

R. P. Williams et al. in *J. Med. Chem.* 13, 773 (1970) reports the preparation and evaluation as anti-inflammatory agents compounds of the following type:

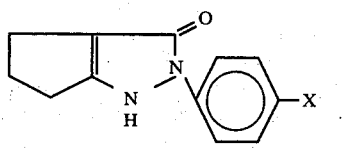

X=H, Br, F.

Although some of the compounds disclosed in the above-cited references are useful as agricultural products, none are taught to be outstanding herbicides. The presence of undesired vegetation is very damaging to useful crops. In the current world situation, wherein food shortages are acute, it is most important not to lose a portion of a valuable crop. The presence of such undesired vegetation results in the loss of a significant portion of such crops. Thus, a need exists for a particularly effective herbicide which will destroy unwanted vegetation.

According to the instant invention, such herbicidal compounds have been discovered.

SUMMARY OF THE INVENTION

This invention relates to novel compounds of Formula I, to agricultural compositions containing them, and to the method of use of these compounds as general herbicides for the pre- or post-emergence control of undesired vegetation.

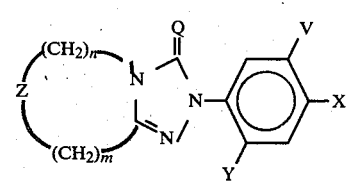

where
- V is hydrogen, fluorine, chlorine, bromine, methyl or OR where R is alkyl of 1–4 carbon atoms;
- X is hydrogen, fluorine, chlorine, bromine, cyano, methyl, methoxy, or nitro;
- Y is hydrogen, fluorine, chlorine, bromine, or methyl:
- n, m is 0, 1, 2, 3 or 4;
- Q is oxygen or sulfur;
- Z is oxygen, $S(O)_p$ or NR';
- p is 0, 1 or 2 and
- R' is alkyl of 1–3 carbon atoms with the provisos that
  (1) n+m=2, 3, or 4; and
  (2) if n+m=2 or 4 then, Y, X≠H
  and when Z is S(O)p, n is 1, 2, 3 or 4.

Preferred for their high herbicidal activity are those compounds of Formula I where, independently:
- Q is oxygen; and
- Z is oxygen, S(O)p or —NR' where R' is alkyl of 1–3 carbon atoms p is 0, 1 or 2 and when Z is S(O)p, n is 1, 2, 3 or 4.

More preferred for their higher herbicidal activity or favorable cost or both are those compounds of the preferred where, independently:

V is hydrogen, chlorine, bromine or OR;
X is fluorine, chlorine or bromine;
Y is fluorine, chlorine, bromine, or methyl;
n+m is 3 and when Z is S(O)p, n≠0.

Most preferred for their excellent herbicidal activity or more favorable cost or both are those compounds of the more preferred where, independently:

V is hydrogen, chlorine or OR;
X is chlorine or bromine; and
Y is fluorine, chlorine or bromine.

Specifically preferred for their outstanding herbicidal activity or highly favorable cost or both are 2-[2,4-dichloro-5-(1-methyethoxy)phenyl]-6,7-dihydro-5H-1,2,4-triazolo[3,4-B][1,3]-oxazin-3-(2H)-one, m.p. 179.5°-180.5°;

2-[2,4-dichloro-5-(1-methylethoxy)phenyl]-5,6,7,8-tetrahydro-8-methyl-1,2,4-triazolo[4,3-A]pyrimidin-3(2H)-one, oil;

2-(2,4-dichloro-5-methoxyphenyl)-6,7-dihydro-5H-1,2,4-triazolo[3,4-B][1,3]-oxazin-3(2H)-one, m.p. 122°-123.5°;

2-[2,4-dichloro-5-(1-methylethoxy)phenyl]-2,5,6,8-tetrahydro-3H-1,2,4-triazolo[3,4-C][1,4]oxazin-3-one, oil.

SYNTHESIS OF THE COMPOUNDS

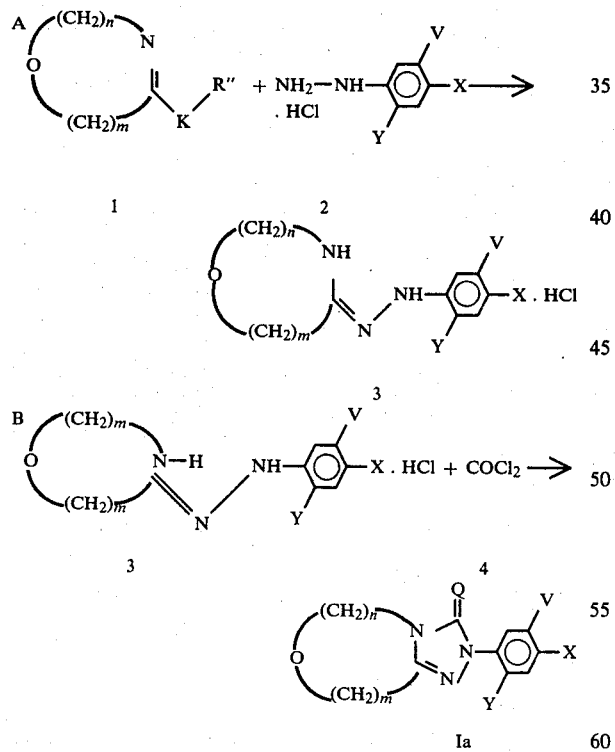

The compounds of Formula I where Z is oxygen (Formula Ia) are prepared as shown in equations A and B. The imino ethers 1 where K can be oxygen or sulfur and R" is a lower alkyl group ($C_1$-$C_8$) especially methyl or ethyl are prepared by methods known in the art. For example, 3-methoxy-5,6-dihydro-2H-oxazine 5 can be prepared according to procedures taught in Chem. Ber. 101, 1979 (1968). 2-Methylthio-5,6-dihydro-4H-1,3-oxazine 6 can be prepared according to methods disclosed in Can. J. Chem. 5,107 (1968). 3-Ethoxy-5,6-dihydro-4H-1, 2-oxazine 7 can be prepared according to procedures taught in Izv. Akad. Nauk. SSSR, Otd. Khim. Nauk 1074 (1962), all of which are herein incorporated by reference.

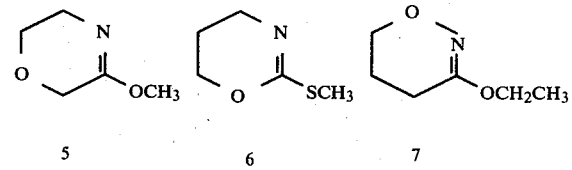

The amidrazone acid salts, e.g., hydrochlorides 3 may be prepared according to methods taught in Belgium Patent Nos. 802,446 and 802,447. The conversion of the amidrazones or their acid salts (e.g. hydrochlorides) 3, to the compounds of Formula Ia is accomplished by reaction with either phosgene (Q in Formula 4 is oxygen) which yields the compounds of Formula Ia wherein Q is oxygen, or thiophosgene (Q in Formula 4 is sulfur) which yields the compounds of Formula Ia wherein Q is sulfur. The reaction is run in a suitable inert organic solvent, e.g. an aromatic hydrocarbon such as benzene or toluene, a chlorinated alkane such as chloroform or methylene chloride, or an ether-type solvent such as tetrahydrofuran. In order to neutralize the acid liberated during the reaction, a suitable base is used, such as a tertiary amine, e.g. pyridine or triethylamine. Ordinary precautions are taken to exclude moisture from the reaction. For completion of the reaction, it is sometimes necessary to heat the reaction mixture to reflux for a period of one to 24 hours. The product of the reaction is isolated by pouring the reaction mixture into water and extracting the product with a suitable solvent, e.g. ether or methylene chloride. The organic extract of the product is dried by addition of a drying agent, e.g. anhydrous sodium sulfate, and the solvent is removed by distillation or evaporation at reduced pressure, leaving the crude product. Purification of the crude material is accomplished by standard techniques, e.g. crystallization, chromatography or distillation.

Many of the compounds of Formula Ia, wherein Q is oxygen, can also be prepared in two steps as shown in Equation c.

c.

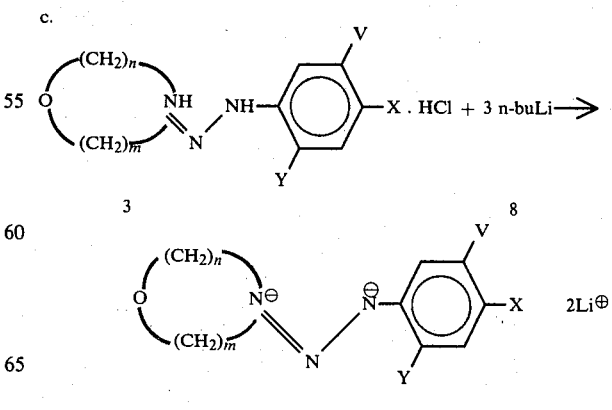

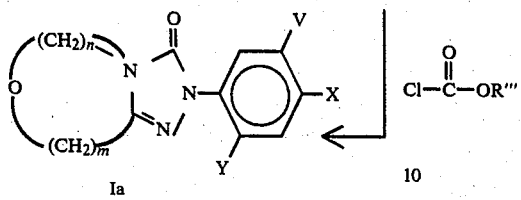

Ia wherein R''' is an alkyl group of 1 to 3 carbon atoms. The amidrazone acid salt 3 in a suitable solvent, e.g. anhydrous tetrahydrofuran, can be reacted with three equivalents of n-butyllithium 8 which generate the amidrazone dianion 9. If the amidrazone free base is used, only two equivalents of n-butyllithium are necessary to generate the dianion 9. Otherwise, in each of the reactions according to Equation c, the same conditions can be used. The reaction temperature is maintained between $-10°$ and $10°$ C. After the addition of n-butyllithium is completed, the reaction is stirred for a brief period (e.g. between 5 and 30 minutes) while maintaining the temperature. One equivalent of an alkyl chloroformate, 10, e.g. methyl chloroformate, is then added, again maintaining the temperature between $-10°$ and $10°$ C. The reaction is completed by stirring at room temperature or refluxing the reaction for a period of one to 24 hours. The product Ia can be isolated as described above.

For amidrazones, which contain a reactive group on the benzene ring, e.g. bromine, cyano or nitro, the butyllithium method of Equation c is not as desirable as the phosgene method described in Equation B.

The compounds of Formula Ib

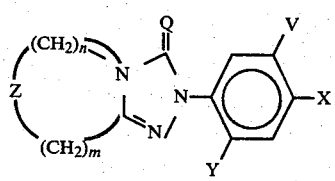

Ib wherein Z is N-R' in Formula I are prepared in a manner analogous to the preparation of compounds of Formula Ia i.e. by either the phosgene-thiophosgene procedure (Equation B) or by the butyllithium procedure (Equation c). The required amidrazones 11 for the preparation of compounds with Formula Ib may be prepared by the imino ether route described above in Equation A. For compounds of Formula 11a wherein n is 2, 3, 4 and m is 0, the imino ether route is not very effective.

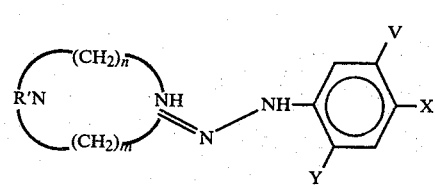

11

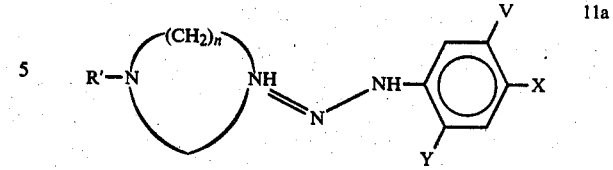

11a

In those cases the amidrazones 11a should be prepared as shown in Equations D. and E.

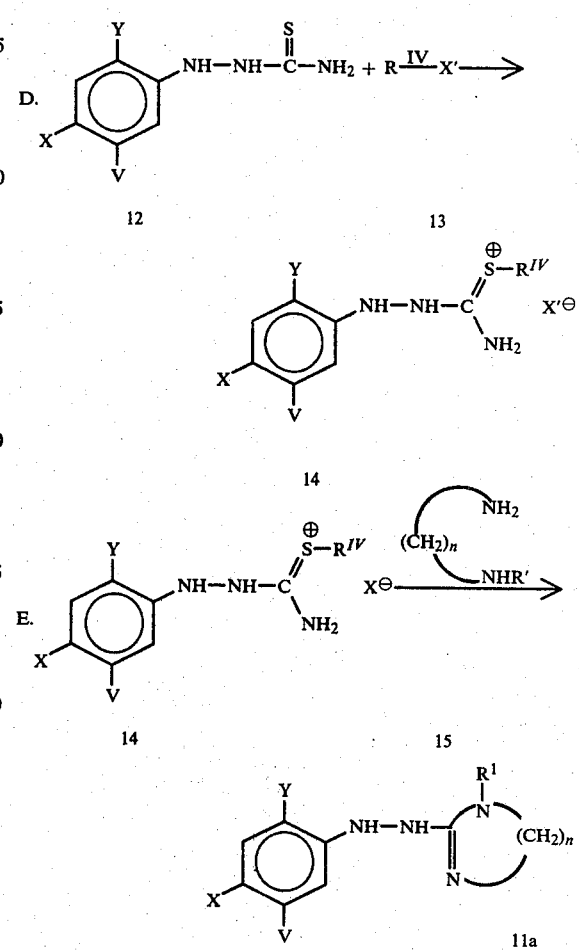

In Equation D, $R^{IV}X'$ is an alkylating agent wherein $R^{IV}$ is a lower alkyl ($C_1$–$C_8$) especially methyl or ethyl and X' is halide (e.g. iodide). Further details of this procedure can be found in the art, e.g. U.S. Pat. No. 3,480,030.

The compounds of Formula Ic, wherein Z is sulfur and Q is oxygen in Formula I

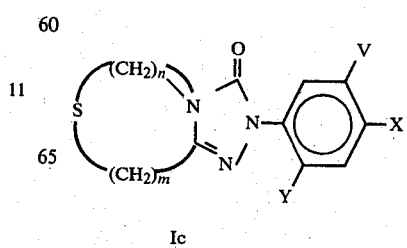

Ic

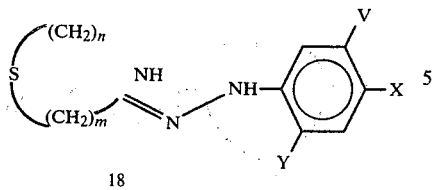

can be prepared from amidrazones 18 by either the phosgene procedure or by the butyllithium-alkylchloroformate procedure described earlier for the preparation of Compounds Ia.

The amidrazones 18 are best prepared by reaction of the iminothioethers 19 in which R''

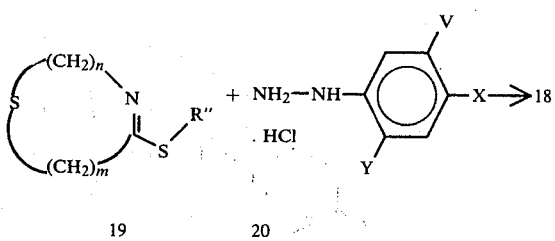

is lower alkyl ($C_1$–$C_8$) especially methyl or ethyl with the appropriate arylhydrazine acid salts 2 (hydrochloride) in a manner similar to that described in Belgium Patent Nos. 802446 and 802447 (Equation F).

The required iminothioethers 19 may be prepared by methods known to those skilled in the art. For example, F. Hamer and R. Rathbone, *J. Chem. Soc.* 243 (1943) describes the preparation of 20 which can be used to prepare compounds of this invention in which n is 3 and m is 0 in Formula Ic.

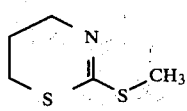

20

When compounds Ic are treated with one equivalent of an oxidizing agent in an appropriate solvent, e.g., metachloroperbenzoic acid in methylene chloride or hydrogen peroxide in acetic acid compounds Id in which Z is SO (p=1) and Q is oxygen in Formula I are produced. (Scheme 1)

Scheme 1

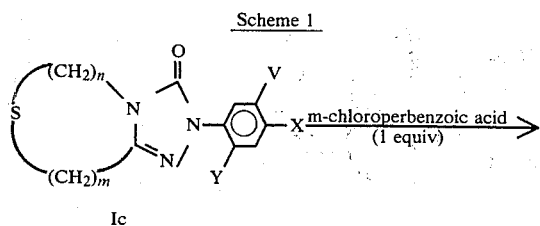

Treatment of Compounds Id with an equivalent of an oxidizing agent results in the formation of Ie in which Z is $SO_2$ and Q is oxygen in Formula I. Compounds Ic are also prepared directly by reaction of Ic with two equivalents of an oxidizing agent as shown in Scheme 1. The reaction of sulfides with oxidizing agents to produce sulfoxides and sulfones is well known in the art. For further details of this procedure see the description by G. Hilgetag and A. Martin in "Preparative Organic Chemistry", Wiley, 1972 pp 667–669 and E. A. Fehnel and M. Carmack in *J. Am. Chem. Soc.* 70, 1813 (1948).

Compounds If in which Z is S(O)p and Q is sulfur in Formula I

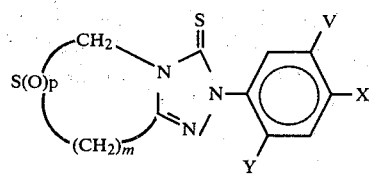

If may be prepared by treatment of amides of Formula Ic, Id or Ie with reagents suitable for converting amides to thioamides e.g. phosphorous pentasulfide. Methods for converting amides to thioamides are well known in the art. Details of this procedure may be found in articles by D. Paquer in *Int. J. Sulfur Chem.*, 8 (1), 173 (1973) and P. Weintraub ibid, 8 (2), 321 (1973).

The following examples further illustrate the preparation of the compounds of this invention. Unless otherwise indicated all parts are by weight and the temperatures in °C.

EXAMPLE 1

Preparation of 2[2,4-dichloro-5-(1-methylethoxy)phenyl]-6,7-dihydro-5H-1,2,4-triazolo[3,4-B][1,3]-oxazine-3(2H)-one 3.5 Parts of the hydrochloride salt of the 2,4-dichloro-5-(1-methylethoxy)phenylhydrazone of 3,4,5,6-tetrahydro-1,3-oxazine-2-one (prepared by methods similar to those described in Belgian Patent Nos. 802446 and 802447) were combined with 75 parts of dry tetrahydrofuran and cooled to −10° under an atmosphere of nitrogen. To this solution 27.1 parts of a solution of 1.6 M n-butyllithium in hexane, purchased from Foote Mineral Company, Exton, Pa., was added dropwise while maintaining the temperature of the reaction between −10° and +10°. The reaction mixture was stirred for about 15 minutes following the addition of n-butyllithium. Then 1.0 part of methyl chloroformate was added dropwise while maintaining the temperature between −10° and +10°. After the addition of the chloroformate was completed the cooling bath was removed and the reaction was allowed to warm to room temperature. It was then stirred for about 30 minutes. The crude reaction mixture was poured into 500 parts of water. The aqueous solution was then extracted 3 times with 200 parts of methylene chloride. The crude extracts were combined and dried over anhydrous sodium sulfate and then filtered. The solvent was removed from the filtrate by evaporation under a reduced pressure of 50–300 mm on a rotary evaporator. The crude product was purified by dry column chromatography on alumina with chloroform; 0.6 parts of material with mp 179.5–180.5 was obtained.

Using a procedure analogous to Example 1 and the appropriate amidrazone or using the phosgene-thiophosgene procedure described earlier, the following compounds of Formula Ia may be prepared (unless otherwise specified "Properties" designates melting point in °C.)

phenyl)hydrazone (prepared by methods similar to those described in U.S. Pat. No. 3,480,630) were added to 150 parts of dry tetrahydrofuran. The mixture was cooled to −10° C. under an atmosphere of nitrogen. To this mixture was added dropwise 100 parts of a solution of 1.6 M n-butyllithium in hexane while maintaining the temperature of the reaction between 0° and −10°. After the addition was completed the reaction was stirred for five minutes. 4.0 parts of methylchloroformate was added dropwise. The temperature was maintained at −10° during the addition. After the addition was completed, the cooling bath was removed. The reaction was stirred for 30 minutes at ambient temperature. The crude reaction mixture was poured into 500 parts of water and concentrated hydrochloric acid was added to the mixture to lower the pH to 7. The crude product was isolated by extraction of the aqueous solution successively with three 200 part portions of methylene chloride. The crude extracts were combined and dried over anhydrous sodium sulfate and then filtered. The solvent was removed from the filtrate by evaporation under a reduced pressure of 50–300 mm on a rotary evaporator. The crude product was purified by dry column chromatography on alumina with 2% ethanol in chloroform. 0.7 parts of product with mp 148°–152° was isolated.

| n | m | Y | X | V | Q | Properties |
|---|---|---|---|---|---|---|
| 2 | 1 | Cl | Cl | H | O | 144–145 |
| 2 | 1 | Cl | Cl | OCH$_3$ | O | 178–179 |
| 2 | 1 | Cl | Cl | OCH(CH$_3$)$_2$ | O | oil-IR bands: 1700 cm$^{-1}$, 1580 cm$^{-1}$. |
| 3 | 0 | Cl | Cl | OCH$_3$ | O | 122–123.5 |
| 3 | 0 | Cl | Cl | H | O | oil-NMR (CDCl$_3$) (δ) 2.3 (m,2H), 4.0 (t,2H), 4.7 (t,2H), 7.9 (m,3H) |
| 3 | 0 | F | Cl | H | O | 116–118 |
| 2 | 1 | Cl | Cl | H | S | |
| 3 | 0 | Cl | Cl | OCH$_3$ | O | |
| 1 | 2 | Cl | Cl | OCH$_2$CH$_3$ | O | |
| 0 | 3 | Cl | Cl | OCH(CH$_3$)$_2$ | O | |
| 4 | 0 | Cl | Cl | O(CH$_2$)$_2$CH$_3$ | O | |
| 0 | 4 | Cl | Cl | O(CH$_2$)$_3$CH$_3$ | O | |
| 2 | 1 | Cl | Cl | OCH$_2$CH(CH$_3$)$_2$ | O | |
| 2 | 1 | Cl | Cl | OCH(CH$_3$)CH$_2$CH$_3$ | O | |
| 2 | 1 | F | F | F | O | |
| 1 | 2 | Cl | Cl | Cl | O | |
| 1 | 2 | Cl | Cl | Br | O | |
| 1 | 2 | H | Cl | Cl | O | |
| 3 | 0 | Br | Br | H | O | |
| 2 | 1 | Cl | NO$_2$ | H | O | |
| 2 | 1 | H | CN | H | O | |
| 2 | 1 | H | H | H | O | |
| 2 | 1 | CH$_3$ | CH$_3$ | CH$_3$ | O | |
| 2 | 1 | CH$_3$ | OCH$_3$ | H | O | |

EXAMPLE 2

Preparation of 2-(2,4-dichlorophenyl)-5,6,7,8-tetrahydro-8-methyl-1,2,4-triazolo[4,3-a]pyrimidin-3-(2H)-one 10.3 Parts of the hydroiodide salt of 3,4,5,6-tetrahydro-1-methyl-2(1H)-pyrimidinone (2,4-dichloro- Using a procedure analogous to Example 2 and the appropriate amidrazone or using thiophosgene-phosgene procedure described earlier and the appropriate amidrazone the following compounds of Formula Ib may be prepared.

| n | m | R' | Y | X | V | Q | Properties |
|---|---|---|---|---|---|---|---|
| 3 | 0 | CH$_3$ | H | Cl | H | O | 218–222 |
| 3 | 0 | CH$_3$ | H | H | H | O | 80–83° |
| 3 | 0 | CH$_3$ | Cl | Cl | OCH(CH$_3$)$_2$ | O | oil-IR bands 1710 cm$^{-1}$, 1620 cm$^{-1}$. |

-continued

| n | m | R' | Y | X | V | Q | Properties |
|---|---|---|---|---|---|---|---|
| 2 | 1 | $CH_2CH_3$ | Cl | Cl | H | S | |
| 3 | 0 | $CH_2CH_2CH_3$ | Cl | Cl | $OCH_3$ | O | |
| 1 | 2 | $CH(CH_3)_2$ | Cl | Cl | $OCH_2CH_3$ | O | |
| 0 | 3 | $CH_3$ | Cl | Cl | $OCH(CH_3)_2$ | O | |
| 4 | 0 | $CH_3$ | Cl | Cl | $O(CH_2)_2CH_3$ | O | |
| 0 | 4 | $CH_3$ | Cl | Cl | $O(CH_2)_3CH_3$ | O | |
| 2 | 1 | $CH_3$ | Cl | Cl | $OCH_2CH(CH_3)_2$ | | |
| 2 | 1 | $CH_3$ | Cl | Cl | $OCH(CH_3)CH_2CH_3$ | O | |
| 2 | 1 | $CH_3$ | F | F | F | O | |
| 1 | 2 | $CH_3$ | Cl | Cl | Cl | O | |
| 1 | 2 | $CH_3$ | Cl | Cl | Br | O | |
| 1 | 2 | $CH_3$ | H | Cl | Cl | O | |
| 3 | 0 | $CH_3$ | Br | Br | H | O | |
| 2 | 1 | $CH_3$ | Cl | $NO_2$ | H | O | |
| 2 | 1 | $CH_3$ | H | CN | H | O | |
| 2 | 1 | $CH_3$ | H | H | H | O | |
| 2 | 1 | $CH_3$ | $CH_3$ | $CH_3$ | $CH_3$ | O | |
| 2 | 1 | $CH_3$ | $CH_3$ | $OCH_3$ | H | O | |

EXAMPLE 3

Preparation of 2-(2,4-dichloro-5-methoxyphenyl)-2,5,6,8-tetrahydro-3H-1,2,4-triazolo [3,4-C][1,4]-thiazine-3-thione

A. Preparation of 2,4,5,6-tetrahydro-1,4-thiazin-3-(4H)-one (2,4-dichloro-5-methoxyphenyl)hydrazone Fluorosulfate salt 3.2 parts of 2,4,5,6-tetrahydro-1,4-thiazin-3-(4H)thione (prepared by methods taught in *Chem. Abs.* 70 1264y) was dissolved in 50 parts of methylene chloride. To this solution kept under an atmosphere of nitrogen and cooled to 10° was added dropwise 2.8 parts of methyl fluorosulfate. The temperature of the reaction was held at 10° during the addition. After the addition of methyl fluorosulfate was completed, the cooling bath was removed and the reaction mixture was allowed to warm to room temperature. 5.0 parts of 2,4-dichloro-5-methoxyphenyl hydrazine was added to the reaction mixture. The reaction mixture was stirred for one hour. The solid precipitate which formed was filtered and washed with 50 parts of diethyl ether. 7.4 parts of material with mp 180°–188° was obtained.

B. Preparation of 2-(2,4-dichloro-5-methoxyphenyl)-2,5,6,8-tetrahydro-3H-1,2,4-triazolo [3,4-C][1,4]-thiazine-3-thione 3.7 parts of the fluorosulfate salt of 2,4,5,6-tetrahydro-1,4-thiazin-3(4H)-one (2,4-dichloro-5-methoxyphenyl)hydrazone was added to 100 parts of dry tetrahydrofuran containing 3.1 parts of triethylamine. To the above mixture was added 1.3. parts of thiophosgene. The mixture was then refluxed for three hours. The crude reaction product which formed was filtered through alumina for dry column chromatography (purchased from ICN Pharmaceuticals, Cleveland, Ohio). The solvent was evaporated from the filtrate at a reduced pressure of 50–300 mm on a rotary evaporator. The residue was crystallized from a mixture of toluene and methylcyclohexane. 0.8 parts of product with mp 131°–135° was obtained.

By using a procedure analogous to Example 3 and the appropriate amidrazone and either phosgene or thiophosgene. The following compounds of Formula I wherein Z is sulfur may be prepared.

| n | m | Y | X | V | Q |
|---|---|---|---|---|---|
| 2 | 0 | Cl | Cl | H | O |
| 2 | 1 | Cl | Cl | $OCH_3$ | O |
| 3 | 0 | Cl | Cl | $OCH_2CH_3$ | O |
| 4 | 0 | Cl | Cl | $OCH(CH_3)_2$ | O |
| 1 | 2 | Cl | Cl | $O(CH_2)_2CH_3$ | O |
| 1 | 3 | Cl | Cl | $O(CH_2)_3CH_3$ | O |
| 3 | 0 | Cl | Cl | $OCH_2CH(CH_3)_2$ | O |
| 3 | 0 | Cl | Cl | $OCH(CH_3)CH_2CH_3$ | O |
| 3 | 0 | F | F | F | O |
| 3 | 0 | Cl | Cl | Cl | O |
| 3 | 0 | Cl | Cl | Br | O |
| 3 | 0 | H | Cl | Cl | O |
| 3 | 0 | Br | Br | H | O |
| 2 | 1 | Cl | $NO_2$ | H | O |
| 3 | 0 | H | CN | H | O |
| 2 | 1 | H | H | H | O |
| 3 | 0 | $CH_3$ | $CH_3$ | $CH_3$ | O |
| 3 | 0 | $CH_3$ | $OCH_3$ | H | O |

Treatment of the compounds of Formula Ic (prepared as described in Example 3) with one equivalent of meta-chloroperbenzoic acid leads to compounds having Formula Id. Treatment of the compounds of Formula Ic with two equivalent of meta-chloroperbenzoic acid leads to compounds of formula Ie. By this procedure the following compounds with Formula Id or Ie may be prepared.

| n | m | Y | X | V | Z |
|---|---|---|---|---|---|
| 2 | 1 | Cl | Cl | $OCH_3$ | SO |
| 3 | 0 | Cl | Cl | $OCH_2CH_3$ | $SO_2$ |
| 4 | 0 | Cl | Cl | $OCH(CH_3)_2$ | $SO_2$ |
| 1 | 2 | Cl | Cl | $O(CH_2)_2CH_3$ | $SO_2$ |
| 1 | 3 | Cl | Cl | $O(CH_2)_3CH_3$ | $SO_2$ |
| 3 | 0 | Cl | Cl | $OCH_2CH(CH_3)_2$ | $SO_2$ |
| 3 | 0 | Cl | Cl | $OCH(CH_3)CH_2CH_3$ | $SO_2$ |
| 2 | 1 | F | F | F | $SO_2$ |
| 2 | 1 | Cl | Cl | Cl | $SO_2$ |
| 2 | 1 | Cl | Cl | Br | $SO_2$ |
| 2 | 1 | H | Cl | Cl | $SO_2$ |
| 2 | 1 | Br | Br | H | $SO_2$ |
| 2 | 1 | Cl | $NO_2$ | H | $SO_2$ |
| 2 | 1 | H | CN | H | $SO_2$ |
| 2 | 1 | H | H | H | $SO_2$ |
| 2 | 1 | $CH_3$ | $CH_3$ | $CH_3$ | $SO_2$ |
| 2 | 1 | $CH_3$ | $CH_3O$ | H | $SO_2$ |

When the compounds of Formula Id and Ie are treated with an equivalent of phosphorous pentasulfide, the following compounds of Formula If in which p is 0, 1 or 2 and Q is sulfur may be prepared.

| n | m | Y | X | V | Z |
|---|---|---|---|---|---|
| 2 | 1 | Cl | Cl | OCH$_3$ | SO |
| 3 | 0 | Cl | Cl | OCH$_2$CH$_3$ | S |
| 4 | 0 | Cl | Cl | OCH(CH$_3$)$_2$ | SO$_2$ |
| 1 | 2 | Cl | Cl | O(CH$_2$)$_2$CH$_3$ | SO$_2$ |
| 1 | 3 | Cl | Cl | O(CH$_2$)$_3$CH$_3$ | SO$_2$ |
| 3 | 0 | Cl | Cl | O(CH$_2$)CH(CH$_3$)$_2$ | SO$_2$ |
| 3 | 0 | Cl | Cl | OCH(CH$_3$)CH$_2$CH$_3$ | SO$_2$ |
| 2 | 1 | F | F | F | SO$_2$ |
| 2 | 1 | Cl | Cl | Cl | SO$_2$ |
| 2 | 1 | Cl | Cl | Br | SO$_2$ |
| 2 | 1 | H | Cl | Cl | SO$_2$ |
| 2 | 1 | Br | Br | H | SO$_2$ |
| 2 | 1 | Cl | NO$_2$ | H | SO$_2$ |
| 2 | 1 | H | CN | H | SO$_2$ |
| 2 | 1 | H | H | H | SO$_2$ |
| 2 | 1 | CH$_3$ | CH$_3$ | CH$_3$ | SO$_2$ |
| 2 | 1 | CH$_3$ | CH$_3$O | H | SO$_2$ |

FORMULATIONS

Useful formulations of the compounds of Formula I include dusts, granules, pellets, solutions, suspensions, emulsions, wettable powders, emulsifiable concentrates and the like. Many of these formulations can be applied directly. Sprayable formulations can be extended in suitable media and used at spray volumes of from a few liters to several hundred liters per hectare. High strength formulations are used primarily for preparing more dilute field strength formulations. The formulations, broadly, contain about 0.05% to 99% by weight of active ingredient(s) and at least one of (a) about 0.01 to 20% surfactant(s) and (b) about 1% to 99.95% solid or liquid diluent(s). More specifically, they will usually contain these ingredients in the following approximate proportions:

|  | Percent by Weight | | |
|---|---|---|---|
|  | Active Ingredient | Diluent(s) | Surfactant(s) |
| Wettable Powders | 5–90 | 1–94 | 1–10 |
| Oil Suspensions, Emulsions, Solutions (including Emulsifiable Concentrates) | 5–50 | 40–95 | 0–15 |
| Aqueous Suspensions | 5–50 | 40–94 | 1–20 |
| Dusts | 0.05–25 | 70–99.95 | 0–5 |
| Granules and Pellets | 0.05–95 | 1–99.95 | 0–15 |
| High Strength Compositions | 90–99 | 1–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook on Insecticide Dust Diluents and Carriers", 2nd. Edn., Dorland Books, Caldwell, N.J. Suitable diluents include finely divided or granular solids classified as attapulgites, botanicals, calcites, diatomites, dolomites, gypsum, kaolinites, limestones, mica, montmorillonoids, phosphates, pyrophyllites, sulfur, sand, talcs, tripolites, vermiculite, and synthetics such as precipitated, hydrated silicon dioxide, precipitated, hydrated calcium silicate, precipitated calcium carbonate and synthetic organics. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers 1975 Annual", MC Publ. Corp., Ridgewood, N.J., as well as Sisely and Wood, "Encyclopedia of Surface Active Agents", Chemical Publ. Col, New York, 1964, list surfactants and recommended uses. All formulations can contain minor amounts of additives to reduce foaming, caking, corrosion, microbiological growth, etc., or to mark visually the area that has been treated.

Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084).

Granules may be made in several ways. For example, the active ingredient may be sprayed onto preformed granular carriers. Suitable preformed granular carriers include those suitable diluents listed earlier having a particle size range from USS Sieve No. 200 (74 microns) to USS Sieve No. 10 (2000 microns). The preferred particle size is from USS Sieve No. 140 (105 microns) to USS Sieve No. 20 (840 microns). Depending upon the nature of the carrier, the active ingredient may remain on the surface of the carrier or be absorbed into the carrier. Usually when the active ingredient remains on the surface of the carrier, a binding agent is used to hold the active ingredient on the surface. The binding agent should bind the active ingredient to the surface well enough so that not more than 10% of the active ingredient is removed during normal shipping and handling operations. Suitable binding agents include materials which are at least partially soluble in any liquid used in the manufacture of the granules and which adhere to the granular surface. Water-soluble binders are preferred. Suitable binders include, but are not limited to, water-soluble polymers such as polyvinylalcohols, polyvinylpyrrolidones, polyoxyethylenes. Other suitable binders include, ligninesulfonates, starches, sugars, and certain surface active agents listed in "McCutcheons' Detergents and Emulsifiers 1975 Annual", MC Publ. Corp., Ridgewood, N.J.

The active ingredient may be sprayed onto the granules as a solution in a suitable solvent, which may or may not be removed from the formulation. If the active ingredient is a liquid, it may be sprayed onto or mixed with the carrier directly. If it is a solid, it may be melted and applied directly as a liquid. If very low strength granules are desired, the active ingredient may be vaporized onto the carrier. Granules may also be prepared by agglomeration techniques. For example, the active ingredient and a finely divided solid diluent may be mixed and agglomerated by techniques known in the art, such as by spraying with a liquid in a fluidized bed or pan granulator. The active ingredient and diluent may also be mixed with other formulation ingredients and pelletized. The pellets may then be crushed to a desired granular size. Pellets may be made by agglomeration techniques. See J. E. Browning, "Agglomeration", *Chemical Engineering*, Dec. 4, 1967, pp. 147ff. and "Perry's Chemical Engineer's Handbook", 4th Edn., McGraw-Hill, N.Y., 1963, pp. 8–59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, Mar. 14, 1967, Col. 5, Line 43 through Col. 7, Line 62, and Ex. 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3, Line 66 through Col. 5, Line 17 and Examples 1–4.

G. C. Klingman, "Weed Control as a Science", John Wiley & Sons, Inc., New York, 1961 pp. 81–96.

J. D. Fryer and S. A. Evans, "Weed Control Handbook", 5th Edn. Blackwell Scientific Publications, Oxford, 1968, pp. 101–103.

EXAMPLE 3

Wettable Powder

| | |
|---|---|
| 2-[2,4-dichloro-5-(1-methylethoxy)-phenyl]-6,7-dihydro-5H-1,2,4-triazolo[3,4-B] [1,3]oxazin-3(2H)-one | 25% |
| Sodium ligninsulfonate | 2% |
| Sodium alkylnaphthalene sulfonate | 2% |
| Synthetic amorphous silica | 3% |
| Kaolinite | 68% |

The ingredients are blended thoroughly, ground in an air mill to produce an average particle size under 15 microns, reblended and sifted through a U.S.S. No. 50 sieve (0.3 mm opening) before packaging.

EXAMPLE 4

Solution

| | |
|---|---|
| 2-[2,4-dichloro-5-(1-methylethoxy)-phenyl]-5,6,7,8-tetrahydro-8-methyl-1,2,4-triazolo[4,3-A]pyrimidin-3(2H)-one | 20% |
| Dimethylformamide | 80% |

The ingredients are combined and stirred to produce a solution, which can be used for low-volume applications.

EXAMPLE 5

Extruded Pellet

| | |
|---|---|
| 2-(2,4-dichloro-5-methoxyphenyl)-6,7-dihydro-5H-1,2,4-triazolo[3,4-B]-[1,3]oxazin-3(2H)-one | 1% |
| Anhydrous sodium sulfate | 10% |
| Crude Calcium ligninsulfonate | 5% |
| Sodium alkylnaphthalenesulfonate | 1% |
| Polyoxyethylene (4 × 10$^6$ average molecular weight) | 1% |
| Calcium/magnesium bentonite | 82% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 6

Emulsifiable Concentrate

| | |
|---|---|
| 2-[2,4-dichloro-5-(1-methylethoxy)-phenyl]-2,5,6,8-tetrahydro-3H-1,-2,4-triazolo[3,4-C] [1,4]oxazin-3-one | 25% |
| Blend of oil soluble sulfonates and polyoxyethylene ethers | 4% |
| Xylene | 71% |

The ingredients are combined and stirred until solution is complete. A fine screen filter is included in packaging operation to insure the absence of any extraneous undissolved material in the product.

EXAMPLE 7

Aqueous Suspension

| | |
|---|---|
| 2-[2,4-dichloro-5-(1-methylethoxy)-phenyl]-6,7-dihydro-5H-1,2,4-triazolo-[3,4-B] [1,3]oxazin-3(2H)-one | 50.0% |
| Polyacrylic acid thickener | 0.3% |
| Dodecylphenol polyethylene glycol ether | 0.5% |
| Disodium phosphate | 1.0% |
| Monosodium phosphate | 0.5% |
| Polyvinylalcohol | 1.0% |
| Pentachlorophenol | 0.4% |
| Water | 46.3% |

The ingredients are ground together in a sand mill to produce particles essentially all under 5 microns in size.

EXAMPLE 8

Wettable Powder

| | |
|---|---|
| 2-(2,4-dichloro-5-methoxyphenyl)-6,7-dihydro-5H-1,2,4-triazolo[3,4-B] [1,3]oxazin-3(2H)-one | 50% |
| Sodium alkylnaphthalenesulfonate | 2% |
| Sodium ligninsulfonate | 2% |
| Synthetic amorphous silica | 3% |
| Kaolinite | 43% |

The ingredients are thoroughly blended, passed through an air mill to produce an average particle size under 15 microns, reblended, and sifted through a U.S.S. No. 50 sieve (0.3 mm opening) before packaging.

EXAMPLE 9

High-Strength Concentrate

| | |
|---|---|
| 2-[2,4-dichloro-5-(1-methylethoxy)-phenyl]-6,7-dihydro-5H-1,2,4-triazolo-[3,4-B] [1,3]oxazin-3(2H)-one | 99% |
| Trimethylnonyl polyethylene glycol ether | 1% |

The surfactant is sprayed on the active ingredient in a blender and the mixture sifted through a U.S.S. No. 40 sieve (0.42 mm openings) prior to packaging. The concentrate may be formulated further for field use.

EXAMPLE 10

Low Strength Granule

| | |
|---|---|
| 2-[2,4-dichloro-5-(1-methylethoxy)- | |

-continued

| | |
|---|---|
| phenyl]-5,6,7,8-tetrahydro-8-methyl-1,2,4-triazolo[4,3-A]pyrimidin-3-(2H)-one | 0.5% |
| Attapulgite granules (low volatile matter; 0.59–0.25 mm., i.e. USS 30–60 mesh size) | 99.5% |

Forty grams of a solution containing 2.5% 2-[2,4-dichloro-5-(1-methylethoxy)phenyl]-5,6,7,8-tetrahydro8-methyl-1,2,4-triazolo[4,3-A]pyrimidin-3(2H)-one dissolved in methyl alcohol are slowly atomized onto a fluidized bed of attapulgite granules (199 gm). Fluidization of the granules is continued after atomization is complete and until all the methyl alcohol is evaporated from the granules. The granules are packaged for use.

EXAMPLE 11

Extruded Pellet

| | |
|---|---|
| 2-(2,4-dichloro-5-methoxyphenyl)-6,7-dihydro-5H-1,2,4-triazolo[3,4-B] [1,3]-oxazin-3(2H)-one | 25% |
| Anhydrous sodium sulfate | 10% |
| Crude Calcium ligninsulfonate | 5% |
| Sodium alkylnaphthalenesulfonate | 1% |
| Calcium/magnesium bentonite | 59% |

The ingredients are blended, hammer milled and moistened with about 10–12% water. The mixture is then extruded as cylinders about 3 mm in diameter which are cut to be about 3 mm long. These pellets may be used directly after drying or the dried pellets may be crushed to pass a U.S.S. No. 20 sieve (0.84 mm opening). The pellets retained on a U.S.S. No. 40 sieve (0.42 mm openings) may be packaged for use and the fines recycled.

EXAMPLE 12

Low Strength Granule

| | |
|---|---|
| 2-[2,4-dichloro-5-(1-methylethoxy)-phenyl]-6,7-dihydro-5H-1,2,4-triazolo[3,4-B] [1,3]oxazin-3(2H)-one | 0.2% |
| Anhydrous sodium sulfate | 10% |
| Crude Calcium ligninsulfonate | 5% |
| Sodium alkylnaphthalenesulfonate | 1% |
| Finely divided attapulgite clay | 83.8% |

The ingredients are blended, hammer milled and placed in a fluidized bed granulator. Water is aspirated into the fluidized bed of powder until small granules are formed. Water aspiration is then stopped but fluidization is continued to dry the formed granules. The granules are removed from the granulator and screened to pass a U.S.S. No. 20 sieve (0.84 mm opening). Granules retained on a U.S.S. N. 40 sieve (0.42 mm opening) are packaged for use. Granules larger than 0.84 mm are ground and recycled. Fines smaller than 0.42 mm are also recycled.

EXAMPLE 13

Extruded Pellet

| | |
|---|---|
| 2-(2,4-dichloro-5-methoxyphenyl)-6,7-dihydro-5H-1,2,4-triazolo[3,4-B]-[1,3]oxazin-3(2H)-one | 0.1% |
| Anhydrous sodium sulfate | 10% |

-continued

| | |
|---|---|
| Crude Calcium ligninsulfonate | 5% |
| Sodium alkylnaphthalenesulfonate | 1% |
| Polyoxyethylene (4 × 10$^6$ average molecular weight) | 1% |
| Calcium/magnesium bentonite | 82.9% |

The ingredients are blended, hammer milled and then moistened with about 12% water. The moist mixture is extruded as cylinders about 1 mm in diameter and about 2 mm long. These small pellets are dried and packaged. They are applied directly.

EXAMPLE 14

Low Strength Granule

| | |
|---|---|
| 2-[2,4-dichloro-5-(1-methylethoxy)-phenyl]-2,5,6,8-tetrahydro-3H-1,2,4-triazolo[3,4-C] [1,4]oxazin-3-one | 0.05% |
| Dimethylformamide | 5% |
| Attapulgite granules (low volatile matter; 0.59–0.25 mm i.e. U.S.S. No. 30–60 mesh size) | 94.95 |

One-tenth of a gram of 2-[2,4-dichloro-5-(1-methylethoxy)phenyl]-2,5,6,8-tetrahydro-3H-1,2,4-triazolo[3,4-C][1,4]oxazin-3-one is dissolved in 9.9 grams of dimethylformamide. This solution is very slowly atomized onto 190.1 grams of a rapidly tumbling bed of the attapulgite granules. After application of the active is complete, the formulation is blended for a few additional minutes. The dimethylformamide is not removed from the formulation. The granules are packaged for use.

EXAMPLE 15

Emulsifiable Concentrate

| | |
|---|---|
| 2-[2,4-dichloro-5-(1-methylethoxy)-phenyl]-5,6,7,8-tetrahydro-8-methyl-1,2,4-triazolo[4,3-A]pyrimidin-3(2H)-one | 10% |
| Blend of oil-soluble sulfonate with polyoxyethylene ethers | 6% |
| Aromatic hydrocarbon solvent with a Tag closed cup flash point between 100 and 115° F. | 84% |

The ingredients are combined and stirred until solution is complete. The solution is filtered through a fine screen filter prior to packaging to remove any extraneous undissolved material.

EXAMPLE 16

Low Strength Granules

| | |
|---|---|
| 2-(2,4-dichloro-5-methoxyphenyl)-6,7-dihydro-5H-1,2,4-triazolo[3,4-B]-[1,3]oxazin-3(2H)-one | 0.1% |
| Sodium ligninsulfonate | 5% |
| Preformed sand granules having a particle size distribution from U.S.S. sieve No. 140 (150 microns) to U.S.S. sieve No. 50 (297 microns) | 94.9% |

0.5 Gram 2-(2,4-dichloro-5-methoxyphenyl)-6,7-dihydro-5H-1,2,4-triazolo[3,4-B][1,3]oxazin-3(2H)-one and 25 gm sodium ligninsulfonate are dissolved in 50 gm water. This solution is slowly sprayed onto a tumbling bed of the sand granules (474.5 g). After spraying is complete, the tumbling granules are warmed to remove the water. The resulting granules are packaged for use.

The compounds of Formula I may be fomulated using the procedures outlined in Examples 3–16.

UTILITY

The compounds of the present invention are useful when applied as pre- and/or post-emergence treatments for broad-spectrum control of a wide variety of weed and brush species growing on industrial sites, storage lots, along fences and building foundations, along railroad and utility rights-of-way, prison perimeter security patrol corridors, etc.

The precise amount of the compounds of the invention to be used in any particular situation will vary widely according to the end result desired. Factors affecting the optimum rate of application include the plant species to be controlled, soil type, formulation used, prevailing weather conditions, foliage density, length of time for which residual activity is desired, etc. Broadly speaking, the compounds are used at levels of about 0.25 to 20 kilograms per hectare, preferably approximately 0.50 to 10 kilograms per hectare. In general, the higher rates of application from within this range will be selected for adverse conditions or where extended persistence in soil is desired.

Herbicidal activity of the subject compounds was discovered in a number of greenhouse tests. Test procedures are described below.

Test A

Seeds of crabgrass (Digitaria spp.), barnyardgrass (Echinochloa crusgalli), wild oats (Avena fatua), Cassia tora, morningglory (Ipomoea spp.), cocklebur (Xanthium spp.), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifoliolate leaf expanding, crabgrass with two leaves, barnyardgrass with two leaves, wild oats with one leaf, cassia with three leaves (including cotyledonary ones), morningglory with four leaves (including the cotyledonary ones), cocklebur with four leaves (including the cotyledonary ones), sorghum with three leaves, corn with three leaves, soybean with two cotylegonary leaves, rice with two leaves, wheat with one leaf, and nutsedge with three-five leaves were sprayed. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following meanings: B=burn; G=growth retardation; C=chlorosis/necrosis; D=defoliation; E=emergence inhibition; and H=formative effects. 6Y indicates abscised flower buds. The ratings for the compounds tested by this procedure are shown in Table 1.

TABLE 1

| COMPOUND | KG/HA | Bush Bean | Cotton | Morning Glory | Cocklebur | Cassia | Nutsedge | Crabgrass | Barnyard Grass | Wild Oats | Wheat | Corn | Soybean | Rice | Sorghum |
|---|---|---|---|---|---|---|---|---|---|---|---|---|---|---|---|
| (structure 1) | 2/5 | 6B | 6B | 1B | 2B | 1B | 1B | 1B 6C | 3B | 1B | 1B | 3B | 2B | 4B | 4B |
| (structure 2) | 2/5 | 3B 6Y | 9B | 10B | 5B | 4D | 3B | 9B | 6B | 3B | 3B | 7B | 7B | 5B | 8B |
| (structure 3) | 2 | 9B | 9B | 10B | 7B | 9B | 5B | 9B | 10B | 8B | 8B | 7B | 8B | 8B | 9B |
|  | 2/5 | 9B | 9B | 8B | 6B | 5B | 3B | 9B | 8B | 5B | 4G | 6B | 8B | 7B | 7B |
| (structure 4) | 2/5 | 7B | 7B | 2B | 1B | 1B | 1B | 2G | 4B | 2B | 1B | 2B | 3B | 3B | 5B |
| (structure 5) | 2/5 | 5B 4H | 9B | 8B | 5B | 3B | 3B | 3B 7H | 6B | 2B | 4B | 6B | 6B | 6B | 7B |

TABLE 1-continued

| Compound | KG/HA | Morning Glory | Cocklebur | Cassia | Nutsedge | Crabgrass | Barnyard Grass | Wild Oats | Wheat | Corn | Soybean | Rice | Sorghum |
|---|---|---|---|---|---|---|---|---|---|---|---|---|---|
| 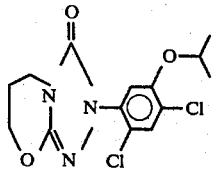 | 2/5 | 9D | 10B | 8B | 3B | 2B | 3B 6C | 3B 8H | 9B | 4B | 3B | 5B | 7B | 8B | 5B |
| 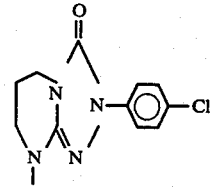 | 2 2/5 | 4B 3B | 5B 4B | 3B 1B | 1B 1B | 1B 1B | 0 0 | 2B 1B | 2D 2B | 1B 1B | 1B 1B | 1B 1B | 2B 1B | 1B 1B | 4B 1B |
| 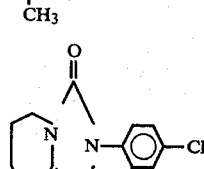 | 2 2/5 | 9B 7B | 9B 7B | 9B 7B | 3B 3B | 4B 3B | 2B 5C 1B | 8B 3B | 9B 5B 8H | 3B 5H 8H | 3B 6H 2B | 3B 6C 3B | 9B 4B | 10C 3B | 3B 6C 3B |
| 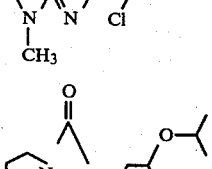 | 2 2/5 | 9B 9B | 9B 9B | 10B 9B | 9B 8B | 2B 4H 3B | 5B 8C 2B 6C | 10B 8B | 10B 10B | 9B 8B | 9B 7B | 9B 8B | 9B 9B | 9B 8B | 9B 9B |
| 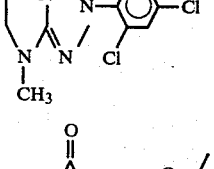 | 2 | 9B | 10B | 10B | 9B | 10B | 10B | 10B | 10B | 9B | 9B | 9B | 9B | 10B | 9B |
| 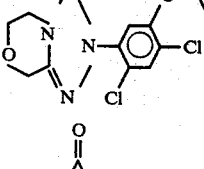 | 2 2/5 | 9B 8B | 8B 8B | 9B 5B | 6B 2B | 6B 4B | 8B 1B | 10B 9B | 10B 7B | 9B 3B | 7B 3B | 9B 7B | 9B 8B | 8B 4B | 9B 6B |
| 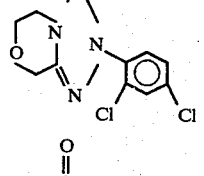 | 2 2/5 | 9B 9B | 9B 8B 7D | 10B 10B | 6B 3B | 4B 7H 8B | 5B 9C | 10B 10B | 10B 10B | 9B 9B | 9B 5B | 5B 9H 5B 9H | 9B 9B | 10B 8B | 9B 9B |

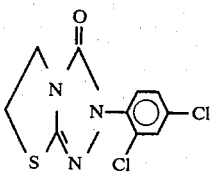

| | | PRE-EMERGENCE | | | | | | | | | | |
|---|---|---|---|---|---|---|---|---|---|---|---|---|
| COMPOUND | KG/HA | Morning Glory | Cocklebur | Cassia | Nutsedge | Crabgrass | Barnyard Grass | Wild Oats | Wheat | Corn | Soybean | Rice | Sorghum |
| 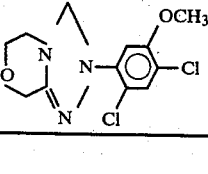 | 2/5 | 0 | 0 | 1C | 0 | 9C | 9C | 9C | 9C | 1C 7H | 1C | 7C | 2C 9H |

TABLE 1-continued

| Structure | | | | | | | | | | | | |
|---|---|---|---|---|---|---|---|---|---|---|---|---|
| thiazine-acetyl with 2,5-dichloro-4-methoxyphenyl | 2/5 | 10C | 10E | 10C | 0 | 10C | 9C | 9C | 7C | 2C 3H | 1C | 4C | 2C 7H |
| oxadiazine-acetyl with 4-chloro-2-fluorophenyl | 2/ 2/5 | 10C 2C 8H | 10C 9C | 10C 10C | 9C 6C | 10C 10C | 10C 10C | 10C 10C | 10C 9C | 9C 9C | 9H 1C 5H | 10C 9C | 10C 9C |
| oxadiazine-acetyl with 2,4-dichlorophenyl | 2/5 | 6C | 1C | 9C | 0 | 10E | 9C | 8C | 9C | 9C | 2C | 7C | 10C |
| oxadiazine-acetyl with 2,5-dichloro-4-methoxyphenyl | 2/5 | 2C 7H | 6G | 2C 7G | 4C | 10C | 10C | 9C | 10C | 9C | 1C 7G | 9C | 10C |
| oxadiazine-acetyl with 2,5-dichloro-4-isopropoxyphenyl | 2/5 | 2C 7H | 6C | 2C 7G | 4C | 10C | 10C | 9C | 10C | 9C | 1C 7G | 9C | 10C |
| N-methyl triazine-acetyl with 4-chlorophenyl | 2 2/5 | 2C 0 | 0 | 0 0 | 10E 3G | 9H 1C | 9C 0 | 3C 8H 0 | 1C 0 | 1C 0 | 1C — | 0 0 | 2C 0 |
| N-methyl triazine-acetyl with 2,4-dichlorophenyl | 2 2/5 | 10C 10C | 9C 5C | 10C 10C | 9C 9G | 10C 10C | 10C 10C | 9C 9C | 10C 10C | 10H 10H | 9H 9H | 9C 2C 7G | 10C 9H |
| N-methyl triazine-acetyl with 2,5-dichloro-4-isopropoxyphenyl | 2 2/5 | 10E 1C 9H | 9C 1C 3H | 10C 5G | 10C 10C | 10C 10C | 10C 10C | 10C 10C | 10C 10C | 10C 10C | 9H 9H | 9C 9C | 10C 10C |
| morpholine-acetyl with 2,5-dichloro-4-isopropoxyphenyl | 2 | 10C | 10C | 10C | 10C | 10C | 10C | 9C | 10C | 10C | 10C | 10C |

TABLE 1-continued

| Structure | Rate | Crabgrass | Barnyardgrass | Sorghum | Wild oats | Johnsongrass | Dallisgrass | Giant foxtail | Ky. bluegrass | Cheatgrass | Corn | Mustard | Cocklebur |
|---|---|---|---|---|---|---|---|---|---|---|---|---|---|
| 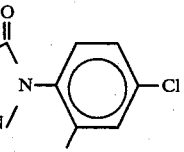 | 2<br>2/5 | 10C<br>1C<br>7G | 10C<br>10C | 10C<br>10C | 10C<br>8C | 10C<br>10C | 10C<br>10C | 10C<br>9C | 10C<br>10C | 10H<br>10H | 10H<br>9H | 10C<br>9C | 10C<br>10C |
| 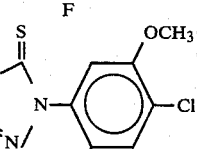 | 2<br>2/5 | 10C<br>10C | 10C<br>9C | 10C<br>10C | 10C<br>10C | 10C<br>10C | 10C<br>10C | 10C<br>10C | 10C<br>10C | 10H<br>10H | 10H<br>9H | 10C<br>9C | 10C<br>10C |

Test B

Two 25-cm plastic bulb pans were filled with fertilized and limed Fallsington silt loam. One pan was planted with corn, sorghum and several grassy weeds. The other pan was planted with soybeans, purple nutsedge (*Cyperus rotundus*), and several broadleaf weeds. The following grassy and broadleaf weeds were planted: crabgrass (*Digitaris sanguinalis*), barnyardgrass (*Echinochloa crusgalli*), wild oats (*Avena fatua*), johnsongrass (*Sorghum halepense*), giant foxtail (*Setaria faberii*), Kentucky bluegrass (*Poa pratensis*), cheatgrass (*Bromus secalinus*), dallisgrass (*Paspalum dilatatum*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12-cm diameter paper pot was also filled with prepared soil and planted with rice and wheat. Another 12-cm pot was planted with sugarbeets. The above four containers were treated preemergence (compound sprayed on soil surface before seed germination).

Twenty-eight days after treatment, the plants were visually rated using the same system as described above for Test A. The data are given in Table II.

TABLE II
FALLSINGTON SILT LOAM

| Structure | Rate, kg/ha | Crabgrass | Barnyardgrass | Sorghum | Wild oats | Johnsongrass | Dallisgrass | Giant foxtail | Ky. bluegrass | Cheatgrass | Corn | Mustard | Cocklebur |
|---|---|---|---|---|---|---|---|---|---|---|---|---|---|
| 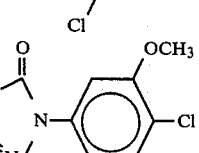 | 0.125<br>0.50 | 3H<br>10H | 2H<br>10H | 0<br>5H | 0<br>6H | 0<br>8H | 2H<br>9H | 0<br>10H | 0<br>9H | 0<br>3H | 0<br>5H | 6H<br>10H | 0<br>0 |
| (second structure) | 0.125<br>0.50 | 0<br>8H | 0<br>3H | 0<br>4H | 0<br>2G | 0<br>6H | 0<br>3H | 0<br>5H | 0<br>2H | 0<br>3H | 0<br>0 | 0<br>8H | 0<br>0 |
| (third structure) | 0.063<br>0.125<br>0.50 | 0<br>9C<br>10C | 0<br>2C<br>8C | 0<br>0<br>7C | 0<br>0<br>3C | 0<br>0<br>8C | 0<br>9C<br>10C | 0<br>3C<br>10C | 0<br>0<br>8C | 0<br>0<br>2C | 0<br>0<br>4H | 2C<br>2C<br>8C | 0<br>—<br>0 |
| (fourth structure) | 0.063<br>0.125<br>0.50 | 8C<br>9C<br>10C | 7C<br>8C<br>10C | 3C<br>4C<br>10C | 0<br>5C<br>9C | 8C<br>6C<br>10C | 9C<br>10C<br>10C | 6C<br>10C<br>10C | 0<br>3C<br>10C | 0<br>0<br>4C | 0<br>0<br>6H | 7C<br>7C<br>10C | 0<br>—<br>— |

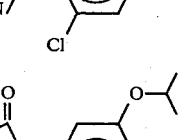

| | Rate, kg/ha | Pigweed | Nutsedge | H. indigo | Morningglory | Cassia | Teaweed | Velvetleaf | Jimsonweed | Soybean | Rice | Wheat | Sugarbeets |
|---|---|---|---|---|---|---|---|---|---|---|---|---|---|

TABLE II-continued

FALLSINGTON SILT LOAM

| Structure | Rate | | | | | | | | | | | | |
|---|---|---|---|---|---|---|---|---|---|---|---|---|---|
| 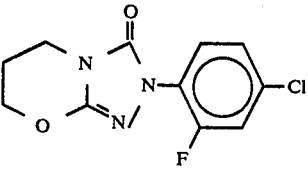 | 0.125<br>0.50 | 0<br>10H | 0<br>0 | —<br>— | 0<br>6H | 0<br>9H | 8H<br>10H | 9H<br>10E | 7H<br>10H | 0<br>0 | 0<br>5H | 0<br>3H | 0<br>3H |
| 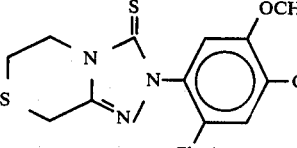 | 0.125<br>0.50 | 0<br>10E | 0<br>0 | —<br>— | 0<br>3H | 0<br>8H | 0<br>3H | 0<br>8H | 0<br>2G | 0<br>0 | 0<br>0 | 0<br>0 | 0<br>7H |
| 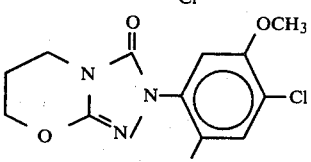 | 0.063<br>0.125<br>0.50 | 0<br>10C<br>10C | 0<br>0<br>2C | —<br>—<br>— | 0<br>0<br>6C | —<br>—<br>— | —<br>—<br>— | —<br>—<br>— | 4C<br>9C<br>10C | 0<br>0<br>2C | 0<br>2C<br>7C | 0<br>0<br>4C | 0<br>4G<br>10C |
| 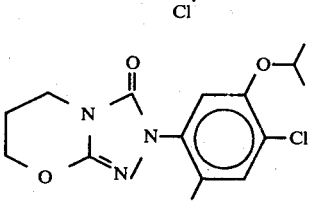 | 0.063<br>0.125<br>0.50 | 3C<br>10C<br>10C | 0<br>0<br>4G | —<br>—<br>— | 0<br>2G<br>8C | —<br>—<br>— | —<br>—<br>— | —<br>—<br>— | 10C<br>10C<br>10C | 0<br>—<br>0 | 0<br>4C<br>9C | 0<br>0<br>3C | 0<br>2G<br>10C |

Test C 25-cm diameter, plastic pots filled with Fallsington silt loam were plant to soybeans, cotton, alfalfa, corn, rice, wheat, sorghum, velvetleaf (*Abutilon theophrasti*), sesbania (*Sesbania exaltata*), cassia (*Cassia tora*), morningglory (*Ipomoea* spp.), jimsonweed (*Datura stramonium*), cocklebur (*Xanthium pennsylvanicum*), crabgrass (*Digitaria* spp.), nutsedge (*Cyperus rotundus*), barnyardgrass (*Echinochloa crusgalli*), giant foxtail (*Setaria faberi*) and wild oats (*Avena fatua*). Eighteen days after planting, the young plants and the soil around them were sprayed overall with the test chemical dissolved in a non-phytotoxic solvent. Fourteen days after treatment, all species were compared to untreated controls and visually rated for response to treatment, again using the above-described scale.

The accordingly obtained data are presented in Table III.

TABLE III

Over-the Top Soil/Foliage Treatment

| Structure | Rate, kg/ha | Soy-beans | Vel-vet-leaf | Ses-ban-ia | Cassia | Cotton | Morn-ing-glory | Al-fal-fa | Jim-son-weed | Cockle-bur |
|---|---|---|---|---|---|---|---|---|---|---|
| 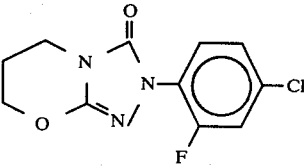 | 0.125<br>0.50 | 3B<br>5B | 9B<br>— | 5B<br>8B | 2B<br>8B | 6B<br>10B | 3B<br>5B | 2B<br>6B | 3B<br>8B | —<br>— |
| 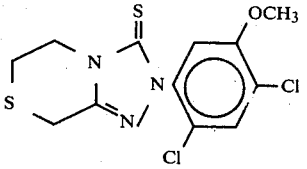 | 0.125<br>0.50 | 5B<br>5B | 9B<br>— | 8B<br>10B | 8B<br>4B | 10B<br>10B | 8B<br>9B | 4B<br>5B | 9B<br>10B | —<br>— |
| 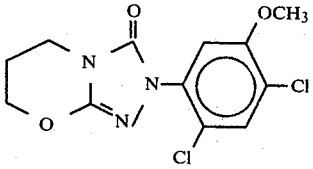 | 0.063<br>0.125<br>0.50 | 2B<br>3B<br>3B | —<br>—<br>10B | 2B<br>5B<br>8B | 0<br>3B<br>4B | 9B<br>10B<br>10B | 2B<br>4B<br>6B | 2B<br>4B<br>6B | 10B<br>10B<br>10B | —<br>2C<br>2B |

TABLE III-continued
Over-the Top Soil/Foliage Treatment

| | Rate, kg/ha | Corn | Crab- grass | Rice | Nut- sedge | Barn- yard- grass | Wheat | Giant Fox- tail | Wild Oats | Sor- ghum |
|---|---|---|---|---|---|---|---|---|---|---|
| | 0.063 | 3B | 4B | 5B | 2B | 10B | 4B | — | 8B | 1C |
| | 0.125 | 5B | — | — | 7B | 10B | 6B | 6B | 10B | 3C |
| | 0.50 | 6B | 10B | — | 10B | 10B | 10B | 6B | 10B | 3C |
| | 0.063 | 3B | 10B | 3B | 2B | 9B | 4B | 2B | 4B | 3B |
| | 0.125 | 4B | 8B | 3B | 2B | 9B | 4B | 2B | 8B | 3B |
| | 0.50 | 4B | 10B | 5B | 4B | 9B | 6B | 6B | 9B | 4B |

| | Rate, kg/ha | Corn | Crab- grass | Rice | Nut- sedge | Barn- yard- grass | Wheat | Giant Fox- tail | Wild Oats | Sor- ghum |
|---|---|---|---|---|---|---|---|---|---|---|
| | 0.125 | 2B | 3B | 0 | 0 | 2B | 0 | 2C | 0 | 3B |
| | 0.50 | 4B | 5B | 3B | 0 | 3B | 2C | 4C | 2C | 3B |
| | 0.125 | 2B | 3B | 3B | 0 | 4B | 2B | 3B | 4B | 3B |
| | 0.50 | 4B | 6B | 5B | 0 | 6B | 3B | 7B | 5B | 3B |
| | 0.063 | 1B | 0 | 2C | 0 | 0 | 0 | 2B | 0 | 2B |
| | 0.125 | 2B | 2C | 3C | 0 | 2B | 2C | 4B | 0 | 4B |
| | 0.50 | 2B | 0 | 5C | 0 | 4B | 3B | 8B | 4B | 4B |
| | 0.063 | 2B | 2B | 0 | 0 | 3B | 2B | 3B | 2B | 2B |
| | 0.125 | 2B | 3B | 3B | 0 | 4B | 2B | 5B | 3B | 4B |
| | 0.50 | 2B | 6B | 6B | 2C | 7B | 4B | 7B | 5B | 7B |
| | 0.063 | 2B | 3C | 3C | 2C | 3C | 2C | 7C | 2C | 3C |
| | 0.125 | 3B | 3C | 2C | 2C | 5C | 5C | 8C | 3C | 4C |
| | 0.50 | 7B | 6C | 6C | 6C | 9C | 6C | 9C | 6C | 9C |

What is claimed is:

1. A compound of the formula

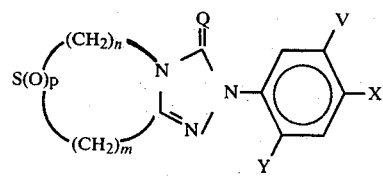

where

V is hydrogen, fluorine, chlorine, bromine, methyl or OR where R is alkyl of 1-4 carbon atoms;

X is hydrogen, fluorine, chlorine, bromine, cyano, methyl, methoxy, or nitro;

Y is hydrogen, fluorine, chlorine, bromine, or methyl;

m is 0,1,2,3, or 4;

n is 1,2,3 or 4;

Q is oxygen or sulfur; and p is 0, 1 or 2 with the proviso that (1) n+m=2, 3, or 4; and (2) if n+m=2 or 4, then Y, X is other than hydrogen.

2. A compound of claim 1 wherein Q is oxygen.

3. A compound of claim 2 wherein

V is hydrogen, chlorine, bromine or OR;

X is fluorine, chlorine or bromine;

Y is fluorine, chlorine, bromine, or methyl; and n+m is 3.

4. A compound of claim 2 wherein

V is hydrogen, chlorine or OR;

X is chlorine or bromine;

Y is fluorine, chlorine or bromine; and n+m is 3.

5. The compound of claim 1 which is 2-(2,4-dichloro-5-methoxyphenyl)-2,5,6,8-tetrahydro-3H-1,2,4-triazolo[3,4-C][1,4]thiazine-3-thione.

6. A composition for the control of undesirable vegetation consisting essentially of a compound of claim 1 and at least one of (a) a surface-active agent and (b) a solid or liquid inert diluent.

7. A composition for the control of undesirable vegetation consisting essentially of a compound of claim 2 and at least one of (a) a surface-active agent and (b) a solid or liquid inert diluent.

8. A composition for the control of undesirable vegetation consisting essentially of a compound of claim 3 and at least one of (a) a surface-active agent and (b) a solid or liquid inert diluent.

9. A composition for the control of undesirable vegetation consisting essentially of a compound of claim 4 and at least one of (a) a surface-active agent and (b) a solid or liquid inert diluent.

10. A method for the control of undesirable vegetation comprising applying to the locus of such undesirable vegetation a herbicidally effective amount of a compound of claim 1.

11. A method for the control of undesirable vegetation comprising applying to the locus of such undesirable vegetation a herbicidally effective amount of a compound of claim 2.

12. A method for the control of undesirable vegetation comprising applying to the locus of such undesirable vegetation a herbicidally effective amount of a compound of claim 3.

13. A method for the control of undesirable vegetation comprising applying to the locus of such undesirable vegetation a herbicidally effective amount of a compound of claim 4.

* * * * *